(12) United States Patent
McElhone et al.

(10) Patent No.: US 10,987,483 B2
(45) Date of Patent: Apr. 27, 2021

(54) BIOMETRIC FEEDBACK AS AN ADAPTATION TRIGGER FOR ACTIVE NOISE REDUCTION, MASKING, AND BREATHING ENTRAINMENT

(71) Applicant: BOSE CORPORATION, Framingham, MA (US)

(72) Inventors: Dale McElhone, Marlborough, MA (US); Jeffrey M. Ellenbogen, Towson, MD (US); Adam C. Furman, Bolton, MA (US); Jonathan Zonenshine, Somerville, MA (US); Christopher R. Paetsch, Cambridge, MA (US); Michael Patrick O'Connell, Northborough, MA (US)

(73) Assignee: BOSE CORPORATION, Framingham, MA (US)

( * ) Notice: Subject to any disclaimer, the term of this patent is extended or adjusted under 35 U.S.C. 154(b) by 223 days.

(21) Appl. No.: 16/132,768

(22) Filed: Sep. 17, 2018

(65) Prior Publication Data

US 2020/0086076 A1   Mar. 19, 2020

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/0476* (2013.01); *A61B 5/4812* (2013.01);
(Continued)

(58) Field of Classification Search
CPC ........ A61M 2230/005; A61M 2230/06; A61M 2230/10; A61M 2230/14; A61M 2230/42;
(Continued)

(56) References Cited

U.S. PATENT DOCUMENTS 5,356,368 A * 10/1994 Monroe ................ A61M 21/00
600/28
2005/0143617 A1* 6/2005 Auphan ............... A61B 5/4815
600/26

(Continued)

FOREIGN PATENT DOCUMENTS

EP      1886707 A1 *   2/2008   ............ A61M 21/00

OTHER PUBLICATIONS

McKinney SM, Dang-Vu TT, Buxton OM, Solet J, Ellenbogen JM (2011) Covert Waking Brain Activity Reveals Instantaneous Sleep Depth. PLoS ONE 6(3): e17351. doi:10.1371/journal.pone.0017351.

(Continued)

*Primary Examiner* — Navin Natnithithadha
*Assistant Examiner* — Sunita Reddy
(74) *Attorney, Agent, or Firm* — Patterson + Sheridan, LLP

(57) ABSTRACT

Aspects of the present disclosure provide methods, apparatuses, and systems for closed-loop sleep protection and/or sleep regulation. According to an aspect, a biosignal parameter and ambient noise are measured. The biosignal parameter is used to determined sleep condition of a subject. The sleep condition is determined based on: (1) one or more of personalized sleep data, (2) historical sleep data collected for a subset of society, or (3) a combination of both. Based on the sleep condition, an arousal threshold is determined. Based on the ambient noise and the determined sleep condition, one or more actions are taken to regulate sleep and avoid sleep disruption by using sound masking or active noise reduction (ANR).

9 Claims, 5 Drawing Sheets

(51) Int. Cl.
*A61B 5/0476* (2006.01)
*A61B 5/04* (2006.01)
*A61B 5/0205* (2006.01)
*A61M 21/00* (2006.01)

(52) U.S. Cl.
CPC .......... *A61B 5/4818* (2013.01); *A61B 5/6803* (2013.01); *A61B 5/0205* (2013.01); *A61B 5/04012* (2013.01); *A61B 5/4809* (2013.01); *A61B 5/4815* (2013.01); *A61M 2021/0027* (2013.01)

(58) Field of Classification Search
CPC .......... A61M 2230/60; A61M 2230/63; A61M 2021/0027; A61M 21/02; A61M 2205/3306; A61M 2205/3317; A61M 2205/332; A61M 2205/3375; A61M 2205/3553; A61M 2205/3592; A61M 2205/52; A61M 2205/702; A61B 5/0205; A61B 5/04012; A61B 5/0476; A61B 5/4806; A61B 5/4809; A61B 5/4812; A61B 5/4815; A61B 5/4818; A61B 5/6803; G10K 11/16; G10K 11/178; H04R 1/00
USPC .................................................... 600/26–28
See application file for complete search history.

(56) References Cited

U.S. PATENT DOCUMENTS

| | | | | |
|---|---|---|---|---|
| 2007/0055115 A1* | 3/2007 | Kwok | .................. | A61B 5/0205 600/300 |
| 2008/0146890 A1* | 6/2008 | LeBoeuf | .................. | A61B 5/11 600/300 |
| 2008/0157956 A1* | 7/2008 | Radivojevic | ......... | A61B 5/6887 340/531 |
| 2008/0243211 A1* | 10/2008 | Cartwright | .......... | G10K 11/175 607/63 |
| 2013/0234823 A1* | 9/2013 | Kahn | ...................... | G16H 40/63 340/3.1 |
| 2014/0067130 A1* | 3/2014 | Pillai | .................... | H05B 47/105 700/275 |
| 2014/0371547 A1* | 12/2014 | Gartenberg | .......... | A61B 5/0048 600/301 |
| 2015/0258301 A1* | 9/2015 | Trivedi | ................ | A61B 5/6898 600/28 |
| 2015/0320588 A1* | 11/2015 | Connor | ................. | A61F 7/0085 607/107 |
| 2016/0015315 A1* | 1/2016 | Auphan | ............... | A61B 5/6892 600/301 |
| 2016/0071526 A1* | 3/2016 | Wingate | .................. | G01S 3/802 704/233 |
| 2016/0082222 A1* | 3/2016 | Garcia Molina | .... | A61B 5/4815 600/27 |
| 2016/0151603 A1* | 6/2016 | Shouldice | .............. | A61B 5/486 600/28 |
| 2016/0166203 A1* | 6/2016 | Goldstein | .......... | A61B 5/02055 600/301 |
| 2016/0199241 A1* | 7/2016 | Rapoport | ............. | G10K 11/175 600/22 |
| 2016/0217672 A1* | 7/2016 | Yoon | .................. | A61B 5/02055 |
| 2017/0200444 A1* | 7/2017 | O'Connell | ........ | G10K 11/17881 |
| 2018/0330811 A1* | 11/2018 | MacAry | .................. | G06Q 50/12 |
| 2019/0073990 A1* | 3/2019 | Moss | .................. | G10K 11/175 |
| 2019/0099009 A1* | 4/2019 | Connor | ................ | A61B 5/0205 |
| 2019/0192069 A1* | 6/2019 | Garcia Molina | .... | A61B 5/4812 |

OTHER PUBLICATIONS

Dang-Vu, Thien Thanh & M McKinney, Scott & Buxton, Orfeu & Solet, Jo & M Ellenbogen, Jeffrey. (2010). Spontaneous brain rhythms predict sleep stability in the face of noise. Current biology. pp. 14 doi:10.1016/j.cub.2010.06.032.

Sleep Disruption due to Hospital Noises A Prospective Evaluation Orfeu M. Buxton, PhD*; Jeffrey M. Ellenbogen, MD*; Wei Wang, PhD; Andy Carballeira, BM; Shawn O'Connor, BS; Dan Cooper, BS; Ankit J. Gordhandas, SB; Scott M. McKinney, BA; and Jo M. Solet, PhD. pp. 11. 2012 American College of Physicians. www.annals.org on Jun. 12, 2012.

International Search Report and Written Opinion for International Application No. PCT/US2019/049523 dated Jul. 6, 2020.

* cited by examiner

BIOMETRIC FEEDBACK AS AN ADAPTATION TRIGGER FOR ACTIVE NOISE REDUCTION, MASKING, AND BREATHING ENTRAINMENT

BACKGROUND

Aspects of the present disclosure generally relate to closed-loop methods, devices, and systems for regulating or protecting a subject's sleep.

Poor sleep may significantly affect a subject's health. Factors leading to sleep disruption include ambient noise, stress, medical conditions, or discomfort. A need exists for assisting a subject to fall asleep and protecting the subject's sleep that, at least partially, addresses the underlying causes of poor sleep without adversely affecting the subject's health in other, unintended ways.

SUMMARY

All examples and features mentioned herein can be combined in any technically possible manner.

Certain aspects provide a method for analyzing at least one biosignal parameter to determine a sleep condition. Based, at least in part, on the determined sleep condition and detected ambient noise in vicinity of a subject, one or more acoustic interventions are introduced in an effort to protect the subject's sleep. Example acoustic interventions include masking ambient noise, introducing and/or adjusting introduced soothing sounds, and/or adaptively applying active noise reduction (ANR).

Certain aspects provide a method for regulating a sleep pattern of a subject. The method includes measuring at least one biosignal parameter of the subject, comparing the at least one biosignal parameter with sleep data to determine a sleep condition of the subject, detecting ambient noise in a vicinity of the subject, adjusting, based on the determined sleep condition, at least one sound in an attempt to regulate the sleep pattern of the subject, and outputting the adjusted at least one sound.

According to aspects, the method further includes determining, based on the determined sleep condition, at least one sound or at least one active noise reduction (ANR) parameter and corresponding values for attempting to regulate the sleep pattern. According to aspects, adjusting the at least one sound comprises adjusting the sound based on the at least one sound or at least one ANR parameter.

According to aspects, the sleep data comprises at least one of: previously-collected sleep statistics for a plurality of other subjects or personalized sleep statistics of the subject. According to aspects, the previously-collected sleep statistics for the plurality of other subjects and personalized sleep statistics map the at least one biosignal parameter to a corresponding sleep condition and corresponding one or more acoustic events that may result in a sleep arousal of the subject. According to aspects, the one or more acoustic events comprise at least one noise parameter and one or more values of the at least one noise parameter that may result in sleep arousal of the subject.

According to aspects, the adjusting comprises adjusting at least one masking parameter or active noise reduction (ANR) parameter to attempt to counter the acoustic event and avoid the sleep arousal of the subject.

According to aspects, the method further comprises developing the personalized sleep statistics of the subject by: measuring the at least one biosignal parameter of the subject during a time period, wherein one or more values of the biosignal parameter are indicative of a sleep arousal of the subject, measuring the ambient noise during the time period, and associating the measured at least one biosignal parameter with the measured ambient noise to determine each instance of the sleep arousal of the subject. According to aspects, for each instance of the sleep arousal, the method includes recording at least one first value of the biosignal parameter before the instance of sleep arousal indicating the sleep condition of the subject and recording an acoustic event associated with the instance of the sleep arousal that caused the sleep arousal.

According to aspects, the at least one biosignal parameter comprises at least one of: a heart rate, heart rate variability, blood-vessel dynamics, respiration rate, electroencephalogram (EEG), electroocoulogram (EOG), electromyogram (EMG), or motion of the subject.

According to aspects, adjusting the sound comprises adjusting at least one of: a spectral content of a masking sound or a sound pressure level of the masking sound.

Certain aspects provide a wearable audio device comprising a transceiver, at least one microphone, at least one biosensor, a processing unit, and at least one speaker. The transceiver is configured to transmit and receive signals, the at least one microphone is configured to detect ambient noise in a vicinity of the audio device, the least one biosensor is configured for measuring at least one biosignal parameter of a subject wearing the audio device, the processing unit is configured to: compare the at least one biosignal parameter with sleep data to determine a sleep condition of the subject and adjust, based on the determined sleep condition, at least one sound in an attempt to regulate a sleep pattern of the subject, and the at least one speaker is configured to output the at least one adjusted sound.

According to aspects, the processing unit is configured to determine, based on the determined sleep condition, at least one masking parameter or at least one active noise reduction (ANR) parameter and corresponding values for attempting to regulate the sleep pattern.

According to aspects, the at least one biosignal parameter comprises at least one of: a heart rate, heart rate variability, blood vessel dynamics, respiration rate, electroencephalogram (EEG), electroocoulogram (EOG), electromyogram (EMG), or motion of the subject.

According to aspects, the processor is configured to adjust the sound by adjusting at least one of a spectral content of a masking sound or a sound pressure level of the masking sound.

According to aspects, the sleep data comprises at least one of: previously-collected sleep statistics for a plurality of other subjects or personalized sleep statistics of the subject. According to aspects, the previously-collected sleep statistics for the plurality of other subjects and personalized sleep statistics map the at least one biosignal parameter to a corresponding sleep condition and corresponding one or more acoustic events that may result in a sleep arousal of the subject.

According to aspects, the one or more acoustic events comprise at least one noise parameter and one or more values of the at least one noise parameter that may result in a sleep arousal of the subject.

According to aspects, the adjusting comprises adjusting at least one masking parameter or active noise rejection (ANR) parameter to attempt to counter the acoustic event and avoid sleep arousal of the subject.

Certain aspects provide a wearable audio device comprising a transceiver, at least one microphone, at least one biosensor, a processing unit, and at least one speaker. The transceiver is configured to transmit and receive signals, the at least one microphone is configured to detect ambient noise in a vicinity of the audio device, the at least one biosensor is configured to measure at least one biosignal parameter of a subject wearing the audio device, the processing unit is configured to compare the at least one biosignal parameter with sleep data to determine a sleep condition of the subject, categorize portions of the ambient noise, and perform at least one of: adjusting, based on the determined sleep condition, at least one masking parameter associated with a masking sound to be used for masking a first portion of the ambient noise, or adjusting at least one enhancing parameter to enhance a second portion of the ambient noise, and the at least one speaker is configured to output at least one of: the adjusted masking sound to be used for masking the first portion of the ambient noise or the enhanced second portion of the ambient noise to alert the subject.

According to aspects, the transceiver is configured to receive one or more selections from the subject for alerts the subject wishes to receive, and the second portion of the ambient noise is associated with at least one of the selections.

According to aspects, the at least one masking parameter comprises at least one of: a spectral content of the masking sound, a sound pressure level of the masking sound, or an active noise reduction (ANR) level.

Advantages of the adaptive biometric feedback based trigger for active noise reduction, masking, and/or breathing entrainment described herein will be apparent from the description and the claims.

DETAILED DESCRIPTION

A sleep assistance device may include features to perform any one of preparing a subject to fall asleep, initiating the subject's sleep, protecting the subject's sleep, and selectively disrupting the subject's sleep. Aspects of the present disclosure provide methods, devices, and systems configured to collect biometric information associated with a subject and adaptively alter a sound output based on the collected information.

Figure 1:
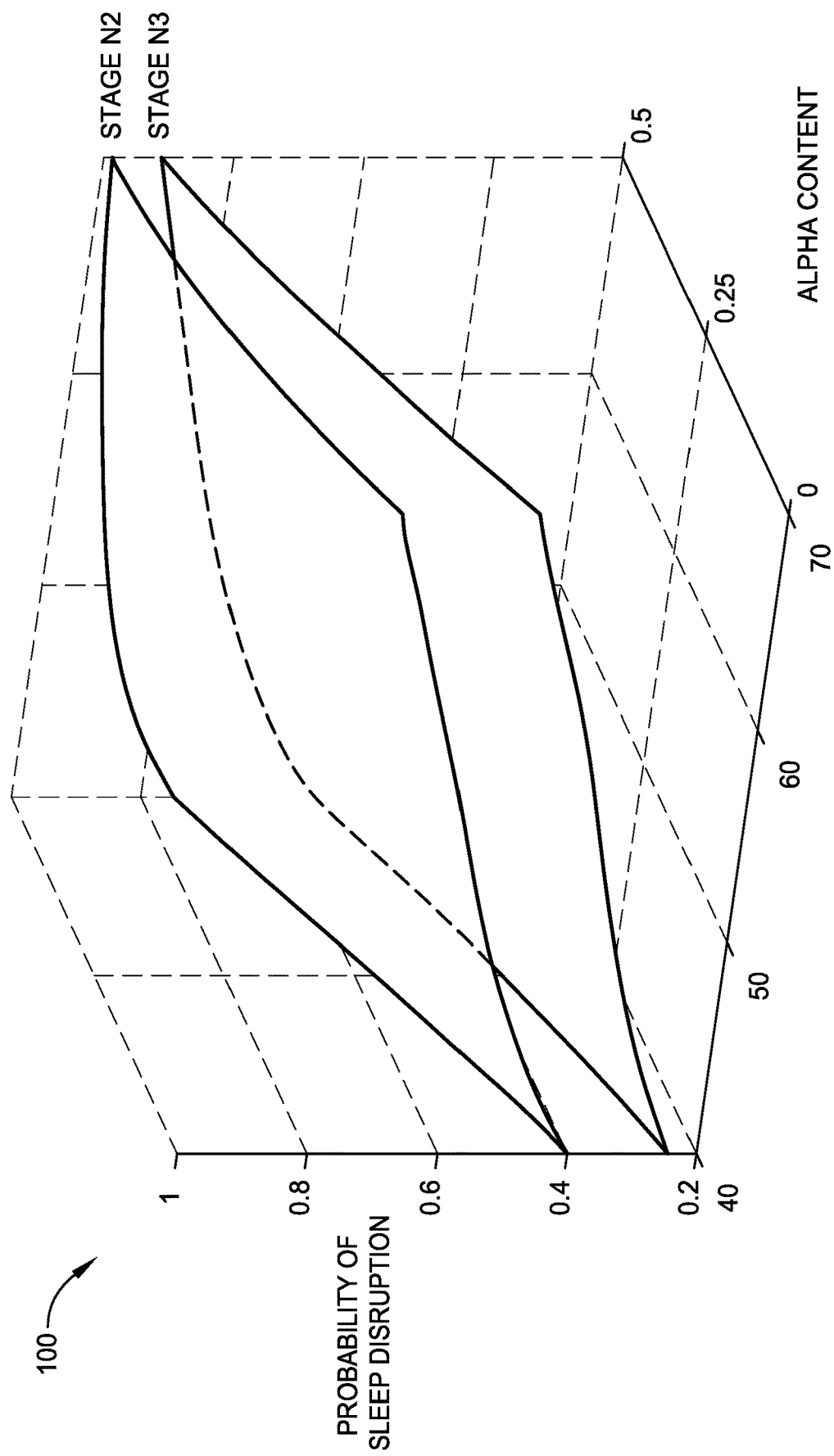
FIG. 1 illustrates an example of sleep fragility as a function of stimulus intensity and EEG alpha content.

FIG. 1 illustrates an example of sleep fragility as a function of stimulus intensity and EEG alpha content. A subject's probability of sleep disruption is based, in part, on a condition of the subject's sleep. A condition of sleep refers to, for example, how deeply the subject is sleeping. As used herein, sleep condition may be referred to as sleep fragility, sleep vulnerability, or terms referring to the likelihood of sleep being disrupted.

In an example, the condition may be associated with sleep stages. Stage N3 sleep is the deepest type of non-rapid eye movement (NREM) sleep. Stage N2 sleep is lighter and more fragile than stage N3 sleep. As illustrated in FIG. 1, for a same sound intensity, a subject has an increased likelihood of sleep disruption when in stage N2 sleep than when in stage N3 sleep.

In an aspect, biometric information collected from the subject is used to approximate the subject's sleep condition. The sleep condition is used to predict the likelihood the subject's sleep may be disrupted. The effect of ambient noises on a sleeping subject varies based on the subject's sleep condition. A same sound is less likely to disrupt a subject in deep sleep as compared to a subject whose sleep is already compromised. Sounds may be adjusted responsive to the condition of the subject's sleep so that a same sound may be masked more when the subject's sleep is compromised as compared to when the subject's sleep is less compromised.

Masking sounds are adjusted based on the subject's determined sleep condition and the ambient noise in the vicinity of the subject. The sound is altered in an effort to adaptively regulate the subject's sleep. As will be described in more detail herein, the sound is altered by one or more of adjusting a sound pressure level of a mask, adjusting a spectral content of a mask, or adjusting active noise reduction (ANR) bandwidth and level to mask (i.e., attempt to cover up the perception of) ambient noise based on the subject's determined sleep condition. According to aspects, the masking reduces the perceived loudness from the environment even if the masking does not remove the perception of ambient noise entirely. In certain aspects, the altered sounds entrain a subject's breathing.

Currently, static masking sounds such as shaped noise or ocean soundscapes attempt to help subjects fall and stay asleep; however, subjects may not enjoy listening to sound while falling asleep and subjects may be exposed to long durations of potentially harmful sound levels. Dynamically adjusting the masking properties based on the sleep condition and the ambient noise mitigates these issues by playing masking sounds to mask at reduced levels or altered spectra when able, based on sleep condition, external noise, or both at a given time. Therefore subjects are exposed to less noise, reducing potential acoustic trauma to the auditory system, as masking is played at a sound level necessary to mask external noise in view of a sleep condition. A correct amount of masking is presented to help prevent sleep disturbance.

Figure 2:
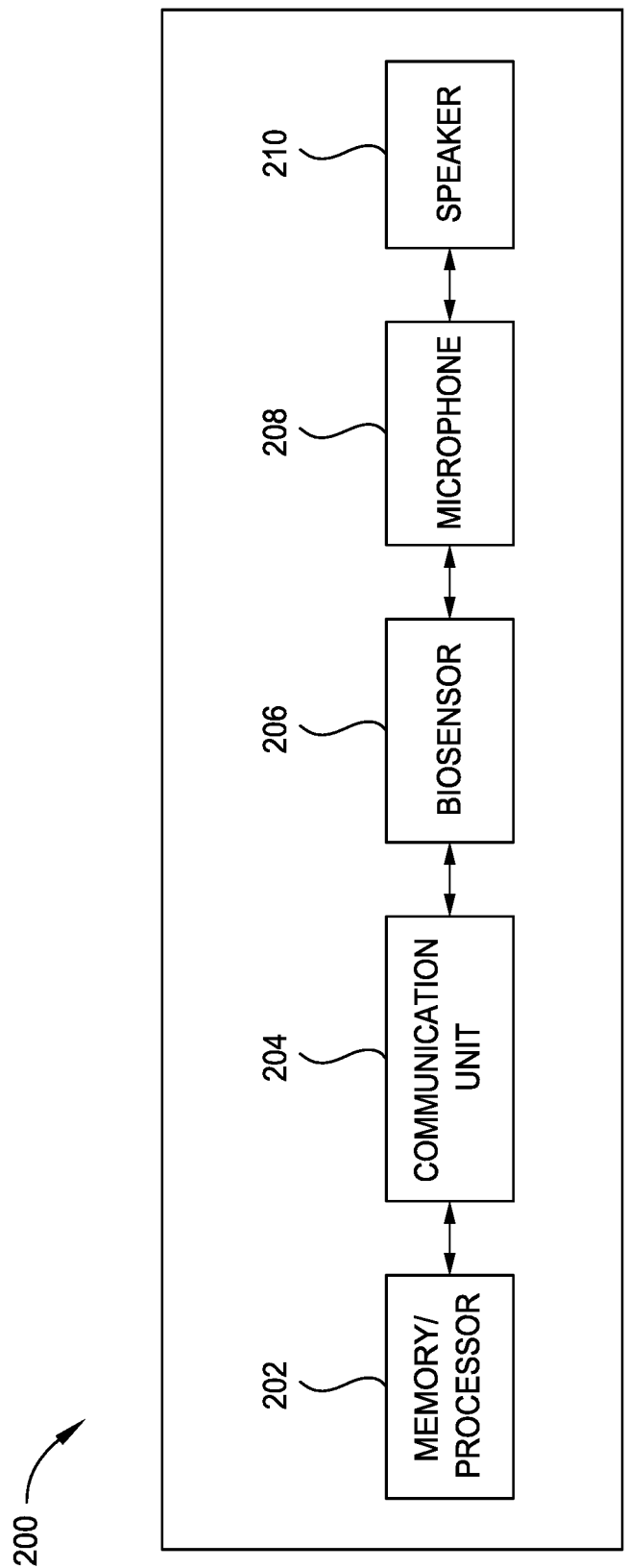
FIG. 2 illustrates an example headphone.

FIG. 2 illustrates an example of a headphone 200. Any or all of the components in FIG. 2 may be combined into multi-function components. A headphone refers to a device that fits around, on, or in an ear and that radiates acoustic energy into the ear canal. Headphones are sometimes referred to as earphones, earpieces, headsets, earbuds, or sport headphones, and can be wired or wireless. In an example, a wearable device may include the components of the headphone 200 and is configured to collect biometric information of a subject and output adjusted sounds in an effort to regulate the subject's sleep. The sounds may be masking sounds with an adjusted sound pressure level and/or adjusted spectral content. Additionally or alternatively, the sounds may entrain breathing in an effort to regulate sleep. Additionally or alternatively, the headphone 200 may adjust an amount of ANR based on the determined sleep condition and ambient noise in an effort to protect sleep.

The memory 202 may include a Read Only Memory (ROM), a Random Access Memory (RAM), and/or a flash ROM. The memory stores program code for controlling the memory and processor 202. The memory and processor 202 control the operations of the headphone 200.

The processor 202 controls the general operation of the headphone. For example, the processor 202 performs process and control for audio and, optionally, data communication. In addition to the general operation, the processor 202 outputs adjusted sounds in an effort to regulate a subject's sleep. The processor 202 is configured to measure, receive, calculate, or detect at least one biosignal parameter of the subject. The processor 202 is configured to compare the biosignal parameter with sleep data in an effort to determine a sleep condition of the subject. The processor 202 is configured to determine, detect, or receive information associated with the ambient noise in the vicinity of the subject. The processor 202 is configured to adjust sound based on the subject's sleep condition and ambient noise. In combination with the speaker 210, the processor 202 is configured to output the adjusted sounds.

The headphone 200 optionally includes a communication unit 204. The communication unit 204, which may be referred to as a transceiver, facilitates a wireless connection with one or more wireless devices, networks, or hub services such as a cloud. The communication unit 204 may include one or more wireless protocol engines such as a Bluetooth engine. While Bluetooth is used as an example protocol, other communication protocols may also be used. Some examples include Bluetooth Low Energy (BLE), Near Field Communications (NFC), IEEE 802.11, or other local area network (LAN) or personal area network (PAN) protocols. The headphone may receive audio files wirelessly via the communication unit 204. Additionally or alternatively, the communication unit 204 may receive information associated with a subject's biosignal parameters, obtained via a contactless sensor. Examples of contactless sensors include a radio frequency (RF) sensor or an under-bed accelerometer.

The headphone 200 optionally includes one or more biosensors 206 used to determine, sense, or calculate a biosignal parameter of a subject wearing the headphone 200. According to an example, the biosensor 206 is one of a photoplethysmography (PPG) sensor, electroencephalogram (EEG) sensor, electrocardiogram (ECG) sensor, electrooculogram (EOG) sensor, electromyogram (EMG) sensor, accelerometer, or a microphone. The biosensor 206 may be any sensor configured to determine, sense, or calculate a subject's biosignal parameter.

According to an aspect, only one earpiece (ear tip, ear cup) of the headphone 200 includes the biosensor 206. In an aspect, neither earpiece includes a biosensor 206. Instead, a biosensor, not on the headphone, may remotely detect a biosignal parameter of the subject. In an example, the biosensor detects fluctuations in small arteries (i.e., arterioles) with a sensor, for example, on the finger to determine blood vessel dynamics, which may help to determine the subject's sleep fragility. In an example, the biosensor may be a contactless biosensor. The contactless biosensor is configured to report detected biosignal parameters to the processor 202, for example, via the communication unit 204.

The headphone 200 optionally includes one or more microphones 208 for ANR, noise cancellation, or communication. In an aspect, the microphones are used to detect the ambient noise in the subject's vicinity.

The speaker or electroacoustic transducer 210 outputs audio signals, including adjusted audio signals in an effort protect the subject's sleep. The transducer 210 is not necessarily a distinct component.

Figure 3:
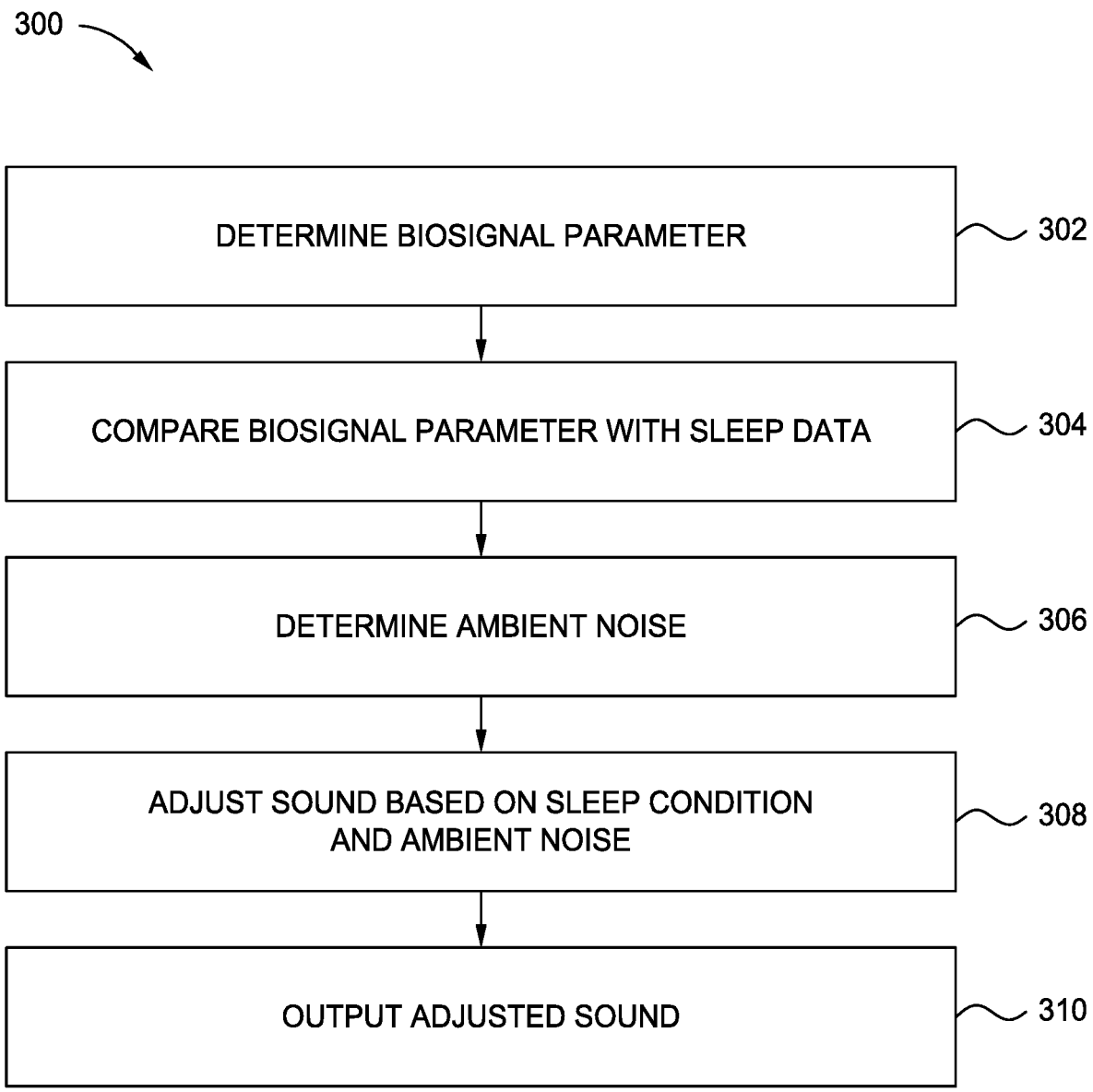
FIG. 3 illustrates an example flow diagram for regulating or protecting a subject's sleep.

FIG. 3 illustrates example operations 300 to regulate a subject's sleep. According to aspects, the method 300 may be performed by the headphone 200. According to aspects, some of the operations are performed by the headphone and others are performed by an external unit, such as a bedside unit.

At 302, the headphone determines, detects, receives, or senses one or more biosignal parameters of the subject wearing the headphone. One or more sensors onboard the headphone may collect the biosignal parameters. In other aspects, a contactless sensor collects the biosignal parameters and transmits the collected biosignal parameters to the headphone, for example, via a wireless connection.

Example biosignal parameters relate to one or more of a respiration rate, optical movement, brain activity, skeletal muscle activity, blood vessel dynamics (which may refer to fluctuations in small arteries), or a subject's movement. In an aspect, different types of biosignal parameters associated with the subject are collected in an effort to determine with increased confidence, the condition of the subject's sleep.

At 304, the at least one biosignal parameter is compared with sleep data in an effort to determine the fragility of the subject's sleep. The sleep data may be based on previously-collected sleep statistics for a subset of society, personalized sleep statistics of the subject, or a combination thereof.

Previously-collected sleep statistics map values of biosignal parameters to a corresponding sleep condition. The sleep data identifies biological signatures within the biosignal parameters such as, for example, heart rate, breathing rate, brain activity, eye movement, muscle activity, or a combination to predict the likelihood that sleep may be disrupted based on a sleep condition.

Sleep statistics also map sleep conditions to acoustic events that lead to arousal for the respective sleep condition. Different conditions of sleep have different sleep arousal thresholds. Based on the sleep condition, corresponding acoustic events associated with an acoustic value may result in sleep disruption or arousal of the subject. Sleep data includes noise values for noise parameters that may result in sleep arousal for corresponding sleep conditions.

Estimating the subject's condition of sleep helps to effectively protect or regulate sleep because subjects have different responses to a same sound or disruption based on the condition of sleep and based on the character of the sound. Assuming the same ambient noise, when a subject's sleep is more fragile, additional masking may help to protect the subject's sleep. When a subject's sleep is less vulnerable, the additional masking may not be necessary to protect sleep. Moreover, the additional masking may cause unintended harmful effects or be undesirable to the subject. Sleep data assists in estimating the subject's sleep condition in an effort to determine how to effectively protect sleep.

At 306, the ambient noise in the vicinity of the subject is determined. In certain aspects, one or more microphones of the headphone determine the ambient noise in the vicinity of the subject. In another aspect, an external unit determines the ambient noise and transmits an indication of the ambient noise to the headphone.

At 308, sound is adjusted based on the sleep condition to mask the ambient noise. As described above, subjects have different responses to a same sound or disruption based on the condition of the sleep. Therefore, the sound is adjusted based on the sleep condition by any combination of varying a sound pressure of a mask, the spectral content of the mask, or the ANR. In an example, a level of noise canceling is adjusted based on the ambient noise and sleep condition in an effort to mask ambient noise.

At 310, the adjusted sound is output in an effort to mask the ambient noise and to help regulate the subject's sleep. Additionally or alternatively, at 310, in aspects, the amount of ANR alters the amount ambient noise heard by the subject. As described herein, sound is adjusted by one or more of adjusting a mask or adjusting ANR.

According to aspects, determining a sleep condition of the subject may be personalized. As described above, at least initially, the subject's sleep condition is based on previously-collected data from other subjects. According to aspects, the headphone or systems described herein are personalized to predict the subject's sleep condition based on subject-specific information. The headphone, via one or more sensors, may monitor when a subject is awoken or when the subject's sleep is disrupted. By tracking information specific to the subject, the headphone is configured to identify patterns to help predict when a subject's sleep may be disrupted in the future. The predictions refine the previously-collected sleep data to personalize sleep protection.

Figure 4:
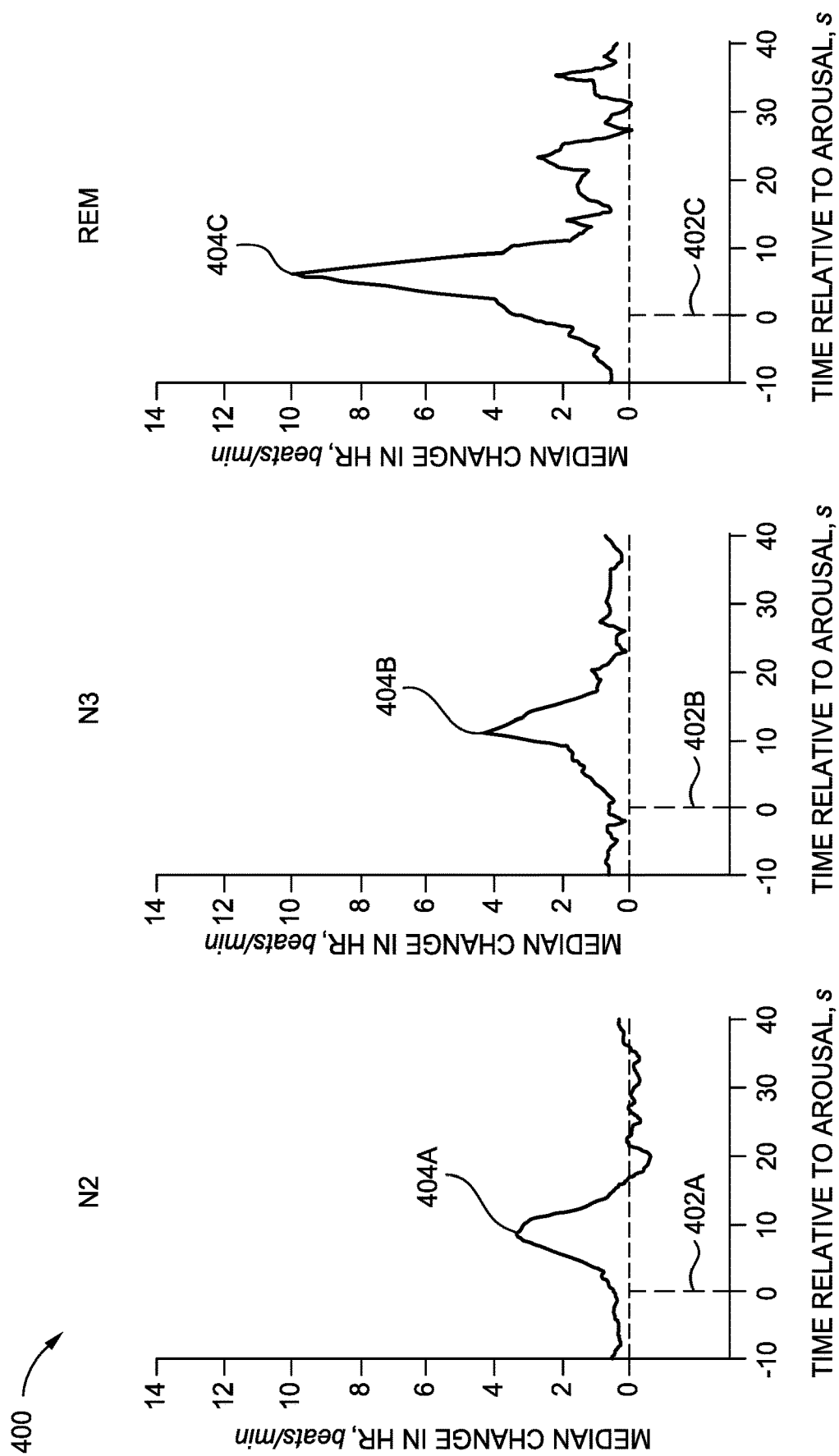
FIG. 4 illustrates example, for various conditions of sleep, changes in heart rate in response to an external stimulus leading to sleep arousal.

FIG. 4 illustrates example changes in heart rate in response to an external stimulus leading to sleep arousal. FIG. 4 illustrates that subjects have varied responses to a sleep arousal based on the condition of the sleep.

A sleep arousal occurs at 402A, 402B, and 402C when subjects are in stage N2, stage N3, and rapid eye movement (REM) sleep, respectively. In response to arousal, heart rates jump in each of the sleep conditions, as shown at 404A, 404B, and 404C. By monitoring when the subject wearing the headphone wakes up, the headphone, or device coupled to the headphone, may intelligently identify signatures within the subject's acoustic environment that are likely to cause sleep disruption. The headphone may refine or personalize the historical sleep statistics based on the subject's personal thresholds to more effectively prevent sleep disturbances. Additionally, or alternatively, by monitoring when the subject wakes up, the headphone or device coupled to the headphone may intelligently identify subject-specific biological signatures or markers within the subject's heart rate or any other monitored biosignal such as breathing rate, brain activity, eye movement, blood vessel dynamics, or any combination thereof, in an effort to more effectively predict the likelihood that sleep may be disrupted. The identified signatures within the subject's acoustic environment, biological signatures of the subject's sleep physiology, or a combination thereof may be used to trigger or change masking and/or ANR in a personalized manner before the subject wakes up.

The sleep conditions illustrated in FIG. 4 are specific stages of sleep; however, the sleep conditions used herein refer more generally to the subject's sleep fragility. Sleep fragility refers to how likely the subject's sleep may be disrupted, sleep vulnerability, or how deeply a subject is sleeping.

FIG. 4 illustrates a heart rate response to a sleep arousal; however any biosignal parameter may be monitored to predict the likelihood that the subject's sleep may be disrupted.

Figure 5:
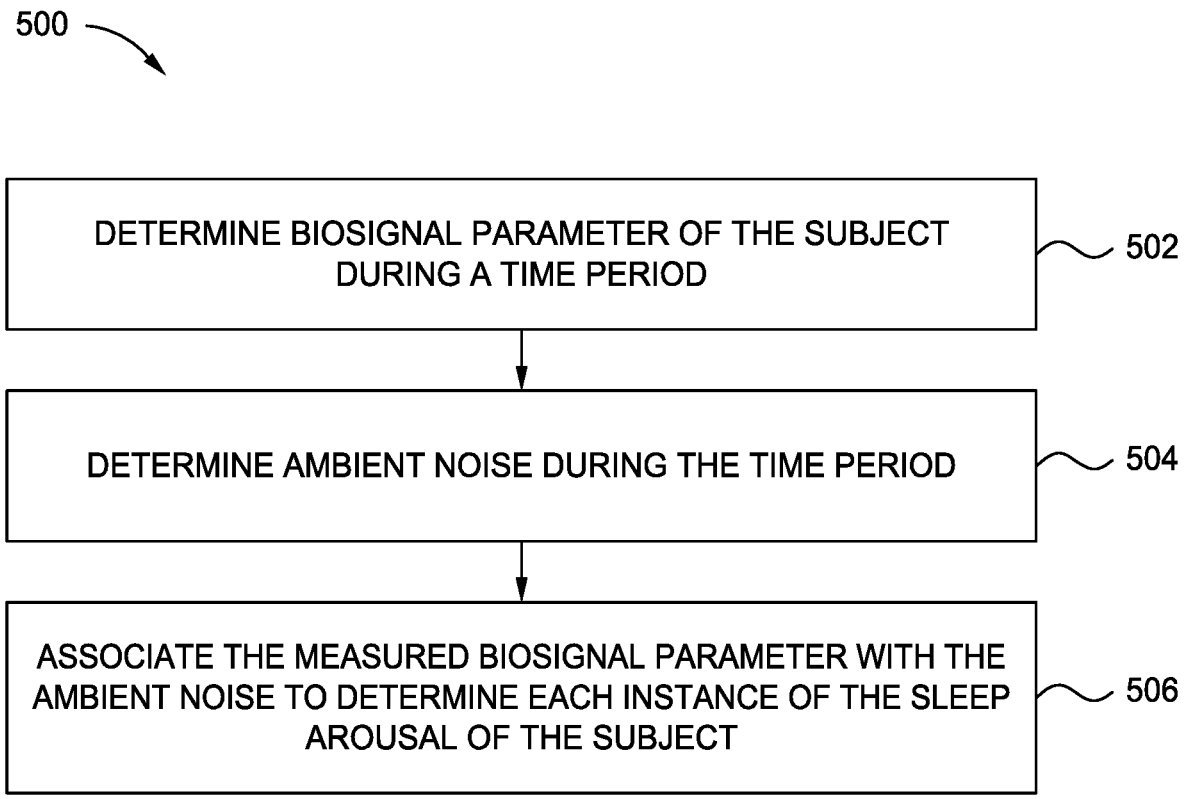
FIG. 5 illustrates an example flow diagram for personalizing sleep data.

FIG. 5 illustrates an example method for personalizing sleep statistics of a subject. The operations 500 may be performed by the headphone 200. According to aspects, some of the operations are performed by the headphone and others are performed by an external unit, such as a bedside unit.

At 502, at least one biosignal parameter of the subject is measured during a time period. One or more values of the biosignal parameter are indicative of a sleep arousal of the subject. As an example, the peak heart rates 404A, 404B, and 404C are example biosignal parameters that indicate a sleep arousal has occurred.

At 504, ambient noise in the vicinity of the subject is determined during the same time period as the detected sleep arousal. Similar to step 306 in FIG. 3, one or more microphones of the headphone measure the ambient noise in the vicinity of the subject. In another aspect, an external unit determines the ambient noise and transmits an indication of the ambient noise to the headphone.

At 506, the measured at least one biosignal parameter is associated with the measured ambient noise to determine each instance of the sleep arousal of the subject.

For each instance of sleep arousal, at least one value of the biosignal parameter before the instance of sleep arousal indicating the sleep state of the subject is recorded. With reference to FIG. 4, the biosignal parameter is recorded for any one or more time instances prior to 404A, 404B, and 404C. For the same instance, an acoustic event and associated acoustic parameter in the vicinity of the subject that may have led to the sleep arousal is also recorded.

The method 500 enables the headphone to determine biomarkers for when the subject's sleep is lightening, such as in a time period before the sleep arousal, or to predict when a sleep arousal may occur for this subject. In response, the sound is adjusted to protect the subject's sleep in an effort to avoid disruption.

A pool of subject-specific data is developed by monitoring the subject's sleep arousals and determining information associated with the sleep arousal as described in FIG. 5. This data modifies the sleep data collected based on a subset of the population to more reliably detect when sleep becomes vulnerable for an individual. Personalized sleep data fine tunes the pool of subject-specific sleep-data to improve the efficacy of the protecting sleep by making it more specific to the individual.

According to aspects, methods of protecting sleep are cut off or stopped based on a subject's selections. The subject may select one or more sounds, notices, or alerts which are not to be masked. For example, the subject may wish to hear fire alarms, security system notifications, a phone ringing, a crying baby, a doorbell, and/or any other audible notification or alarm. The subject may program the headphone to recognize these desired sounds. The headphone may refrain from masking these detected sounds or from applying ANR in the presence of these detected sounds.

According to aspects, the subject may program the headphone to recognize undesired sounds which may be specific to the subject's environment. In an example, the subject may program the headphone to recognize a crying baby, a snoring companion, or garbage trucks. The headphone may mask or noise-cancel (in examples, partially noise-cancel) these detected sounds.

According to an aspect, the desired and undesired sounds may be programmed by any combination of selecting these sounds from a library or recording real-life examples of the sounds for input to the headphone. The subject may categorize sounds as desired or undesired. The headphone is configured to analyze components of the ambient noise to identify the selected sounds and categorize them as desired or undesired sounds based on the subject's selections. The headphone masks the undesired sounds or applies a higher level of ANR for undesired sounds and does not mask the desired sounds or applies a lower level of ANR for desired sounds. Accordingly, selected portions of the ambient noise are selectively masked or are not masked.

In addition to categorizing sounds as desired and undesired, the subject can identify sounds that should be enhanced. For example, a subject may need to hear a crying baby or any other audible notification or alarm at certain times. The subject may program the headphone to recognize these sounds and enhance them upon detection.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

The invention claimed is:

1. A method for regulating a sleep pattern of a subject, comprising:
    measuring, using a biosignal sensor, a rate of change of at least one biosignal parameter of the subject;
    determining, using a processor, a sleep condition of the subject based on the rate of change of the at least one biosignal parameter and sleep data of the subject, the sleep condition associated with a sleep stage that subjects the subject to a noise disturbance level higher than a rapid eye movement (REM) sleep stage associated noise disturbance level, wherein the rate of change is non-zero and less than five units per ten seconds, starting from an onset of the noise disturbance until peaking, wherein the unit comprises beats per minute;
    detecting, using an audio sensor, ambient noise in a vicinity of the subject; and
    adjusting via an output of at least one speaker, based on the determined sleep condition, at least one sound to regulate the sleep pattern of the subject to offset the noise disturbance level.

2. The method of claim 1, further comprising:
    determining, based on the determined sleep condition, at least one sound parameter or at least one active noise reduction (ANR) parameter and corresponding values for used regulate the sleep pattern,
    wherein adjusting via an output of at least one speaker, based on the determined sleep condition, at least one sound to regulate the sleep pattern of the subject to offset the noise disturbance level comprises adjusting the sound based on the at least one sound parameter or at least one ANR parameter.

3. The method of claim 1, wherein the sleep data comprises at least one of: previously-collected sleep statistics for a plurality of other subjects or personalized sleep statistics of the subject.

4. The method of claim 3, wherein the at least one of previously-collected sleep statistics for the plurality of other subjects or the personalized sleep statistics map the at least one biosignal parameter to a corresponding sleep condition and corresponding one or more acoustic events that result in a sleep arousal of the subject.

5. The method of claim 4, wherein the one or more acoustic events comprise at least one noise parameter and one or more values of the at least one noise parameter that results in sleep arousal of the subject.

6. The method of claim 4, wherein the adjusting comprises adjusting at least one masking parameter or active noise reduction (ANR) parameter used to counter the acoustic event and avoid the sleep arousal of the subject.

7. The method of claim 3, further comprising developing the personalized sleep statistics of the subject by:
    measuring the at least one biosignal parameter of the subject during a time period, wherein one or more values of the biosignal parameter are indicative of a sleep arousal of the subject;
    measuring the ambient noise during the time period; and
    associating the measured at least one biosignal parameter with the measured ambient noise to determine each instance of the sleep arousal of the subject,
    for each instance of the sleep arousal:
        record at least one first value of the biosignal parameter before the instance of the sleep arousal indicating the sleep condition of the subject; and
        record an acoustic event associated with the instance of the sleep arousal that caused the sleep arousal.

8. The method of claim 1, wherein the at least one biosignal parameter comprises at least one of: a heart rate, a heart rate variability, blood-vessel dynamics, a respiration rate, an electroencephalogram (EEG), an electroocoulogram (EOG), an electromyogram (EMG), or a motion of the subject.

9. The method of claim 1, wherein adjusting via an output of at least one speaker, based on the determined sleep condition, at least one sound to regulate the sleep pattern of the subject to offset the noise disturbance level comprises adjusting at least one of: a spectral content of a masking sound or a sound pressure level of the masking sound.

* * * * *